United States Patent
Al-Rashdan (10) Patent No.: US 8,251,942 B1
(45) Date of Patent: Aug. 28, 2012

(54) SYSTEM AND METHOD FOR REMOVING BLOOD CONTAINING CONTRAST DYE

(76) Inventor: Ibrahim Rashid Al-Rashdan, Qortoba (KW)

( * ) Notice: Subject to any disclaimer, the term of this patent is extended or adjusted under 35 U.S.C. 154(b) by 0 days.

(21) Appl. No.: 13/330,601

(22) Filed: Dec. 19, 2011

(51) Int. Cl.
*A61M 37/00* (2006.01)
*A61M 29/00* (2006.01)

(52) U.S. Cl. ............... 604/6.09; 604/4.01; 604/6.16; 604/101.01; 604/103.07

(58) Field of Classification Search ............... 604/4.01, 604/5.01, 5.04, 6.09, 6.11, 96.01, 101.01, 604/103.07, 6.16
See application file for complete search history.

(56) References Cited

U.S. PATENT DOCUMENTS

| | | | |
|---|---|---|---|
| 4,714,460 A * | 12/1987 | Calderon | 604/28 |
| 4,781,677 A * | 11/1988 | Wilcox | 604/28 |
| 4,820,261 A | 4/1989 | Schmoll et al. | |
| 5,167,623 A * | 12/1992 | Cianci et al. | 604/43 |
| 5,209,717 A * | 5/1993 | Schmoll et al. | 604/5.01 |
| 5,273,526 A * | 12/1993 | Dance et al. | 604/35 |
| 5,411,479 A * | 5/1995 | Bodden | 604/101.03 |
| 5,919,163 A * | 7/1999 | Glickman | 604/101.05 |
| 6,554,819 B2 | 4/2003 | Reich | |
| 6,585,689 B1 | 7/2003 | Macoviak et al. | |
| 6,699,231 B1 * | 3/2004 | Sterman et al. | 604/509 |
| 7,163,520 B2 | 1/2007 | Bernard et al. | |
| 7,824,357 B2 * | 11/2010 | Al-Rashdan | 604/6.09 |
| 2010/0274189 A1 | 10/2010 | Kurth et al. | |
| 2011/0172558 A1 | 7/2011 | Shapland et al. | |
| 2011/0251555 A1 | 10/2011 | Ducharme et al. | |

FOREIGN PATENT DOCUMENTS

WO   WO 02/060511 A2   8/2002

* cited by examiner

*Primary Examiner* — Leslie Deak
(74) *Attorney, Agent, or Firm* — Richard C. Litman (57) ABSTRACT

The system for removing blood containing contrast dye includes an inner catheter having a fixed proximal end and a distal free end, and an outer catheter coaxially disposed around a portion of the inner catheter, defining an inner channel and an annular outer channel. The fixed end of the inner catheter is coincident with the proximal end of the outer catheter, and the distal end of the inner catheter extends outward from the outer catheter. An annular suction orifice is defined between the distal end of the outer catheter and the inner catheter. First and second balloons are mounted adjacent the distal ends of the outer and inner catheters. The distal free end of the inner catheter extends beyond the second balloon. In use, the first and second balloons are inflated in the coronary sinus and blood containing contrast dye is then removed from between the first and second balloons.

10 Claims, 8 Drawing Sheets

SYSTEM AND METHOD FOR REMOVING BLOOD CONTAINING CONTRAST DYE

BACKGROUND OF THE INVENTION

1. Field of the Invention

The present invention relates to coronary angioplasty devices and procedures, and particularly to a system and method for removing blood containing contrast media, or dye, that provides for the removal of the contrast media used during angioplasty procedures from the coronary sinus of a patient's heart before the blood containing the media enters the right atrium and circulates through the bloodstream to the kidneys, potentially causing contrast-induced nephropathy (CIN).

2. Description of the Related Art

Percutaneous transluminal coronary angioplasty is frequently used in treating coronary atherosclerosis, which produces areas of blockage within a coronary artery. However, prior to performing percutaneous transluminal coronary angioplasty, and during the procedure itself, iodine containing dye or other contrast material is injected into a patient's coronary arteries through a catheter. This iodine solution is fluorescent and enables the coronary arteries to be clearly illustrated for the physician.

A serious problem associated with the use of such contrast solutions exists. The use of such solutions may lead to contrast-induced nephropathy. Contrast-induced nephropathy can result in transient or permanent renal impairment or failure of a patient's kidneys. It is well known that renal dysfunction is associated with the use of radiographic contrast media, and that the dysfunction may range from a transient slight increase in serum creatinine levels to renal failure requiring transient or long-term dialysis.

Many patients require revascularization of more than a single vessel. However, when there is danger of contrast-induced renal failure, the vessels are operated on in separate procedures at greatly increased cost and additional risk of arterial puncture. Therefore, it is highly desirable or imperative to eliminate the risk of renal failure.

Further, there are many other patients with chronic renal insufficiencies who must wait 24 to 48 hours in the hospital before undergoing percutaneous transluminal coronary angioplasty in order to space the kidney load associated with the contrast load. Still others, particularly the elderly with a pre-existing renal insufficiency, make up a large group in which angioplasty is avoided due to multi-vessel disease and multi-vessel intervention, which may lead to renal failure.

Contrast-induced nephropathy can be prevented if the contrast solution is kept away from the kidney. However, once the dye has been mixed with blood, the conventional method to separate the two is by filtration (for example, through dialysis). Dialysis relies on diffusion down a concentration gradient and is not completely effective if the concentration of dye in the blood to be filtered is low. Furthermore, the flow rates of conventional hemodialysis procedures are too high for patients who are undergoing angioplasty, and these patients typically do not tolerate wide fluctuations in blood pressure, as is common with hemodialysis.

Thus, a system and method for removing blood containing radiographic contrast media from the venous system of the heart before the blood circulates to the kidneys is desired for solving the aforementioned problems.

SUMMARY OF THE INVENTION

The system and method for removing blood containing radiographic contrast media used for angioplasty procedures relates to the removal of blood containing contrast dye solution from the coronary sinus of the patient's heart before the blood containing the dye enters the right atrium and circulates through the bloodstream to the kidneys, potentially causing contrast-induced nephropathy (CIN). The system for removing blood containing contrast dye includes an inner catheter, having opposed fixed and free ends, and an outer catheter. The inner catheter is partially disposed coaxially within the outer catheter, defining inner and outer channels. The fixed proximal end of the inner catheter is positioned within the outer catheter, and the distal end of the inner catheter partially extends outward from the outer catheter. An annular suction orifice is defined between the outer catheter and the inner catheter at the distal end of the outer catheter. A guide may be further provided for covering the annular suction orifice and holding the inner catheter in place with respect to the outer catheter. The guide has openings or apertures formed therethrough, allowing blood containing the contrast dye to be suctioned therethrough.

A first balloon is mounted on the outer catheter adjacent the annular suction orifice, and a second balloon is mounted on the inner catheter adjacent the distal free end thereof, the suction orifice being disposed between the two balloons. The distal free end of the inner catheter extends beyond the second balloon. A first lumen is in communication with the first balloon, and the first lumen terminates in a first inflation port. Similarly, a second lumen is in communication with the second balloon, and the second lumen terminates in a second inflation port. A third lumen is in communication with the outer channel and annular suction orifice for draining blood from between the first and second balloons. The third lumen terminates in a first suction port. A fourth lumen communicates with the inner channel of the inner catheter to drain contrast dye from beyond the second balloon, and is attached to a second suction port. The free end of the inner catheter may have a plurality of openings or apertures formed through a sidewall thereof. Thus, if the free end contacts the wall of the coronary sinus and becomes blocked, or is otherwise blocked, the blood containing the contrast dye can still be suctioned through the openings or apertures.

In use, the catheters, which have a curvature that facilitates the insertion of the system in the coronary sinus, are inserted into the coronary sinus, the outer catheter extending to the ostium and the inner catheter extending into the sinus. The first and second balloons are inflated after introducing a contrast solution into a patient's blood stream. Blood containing contrast solution from between the first and second balloons is then removed. The second balloon is inflated first in order to anchor the inner catheter in place in the coronary sinus, the free end thereof being positioned adjacent the patient's lateral vein. Preferably, the inner catheter is formed from a softer material than the outer catheter, thus allowing the outer catheter to be used for positioning, and preventing damage to the inner wall of the coronary sinus vein.

The larger first balloon is inflated in the right atrium, forming a seal at the ostium of the coronary sinus, forming a vacuum between the first and second balloons. The blood containing the contrast solution is then removed from between the inflated first and second balloons by suction through the annular suction orifice into the outer channel formed between the first and second catheters, and blood containing the contrast dye is also removed distal to the second balloon by suction through the inner channel defined by the inner catheter. The first and second balloons are deflated when the blood containing the contrast solution from between the first and second balloons has been removed. The blood containing the contrast dye is drained from the patient.

The physician may optionally choose to filter the blood containing the contrast dye to remove the dye and return the filtered blood to the patient's bloodstream.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
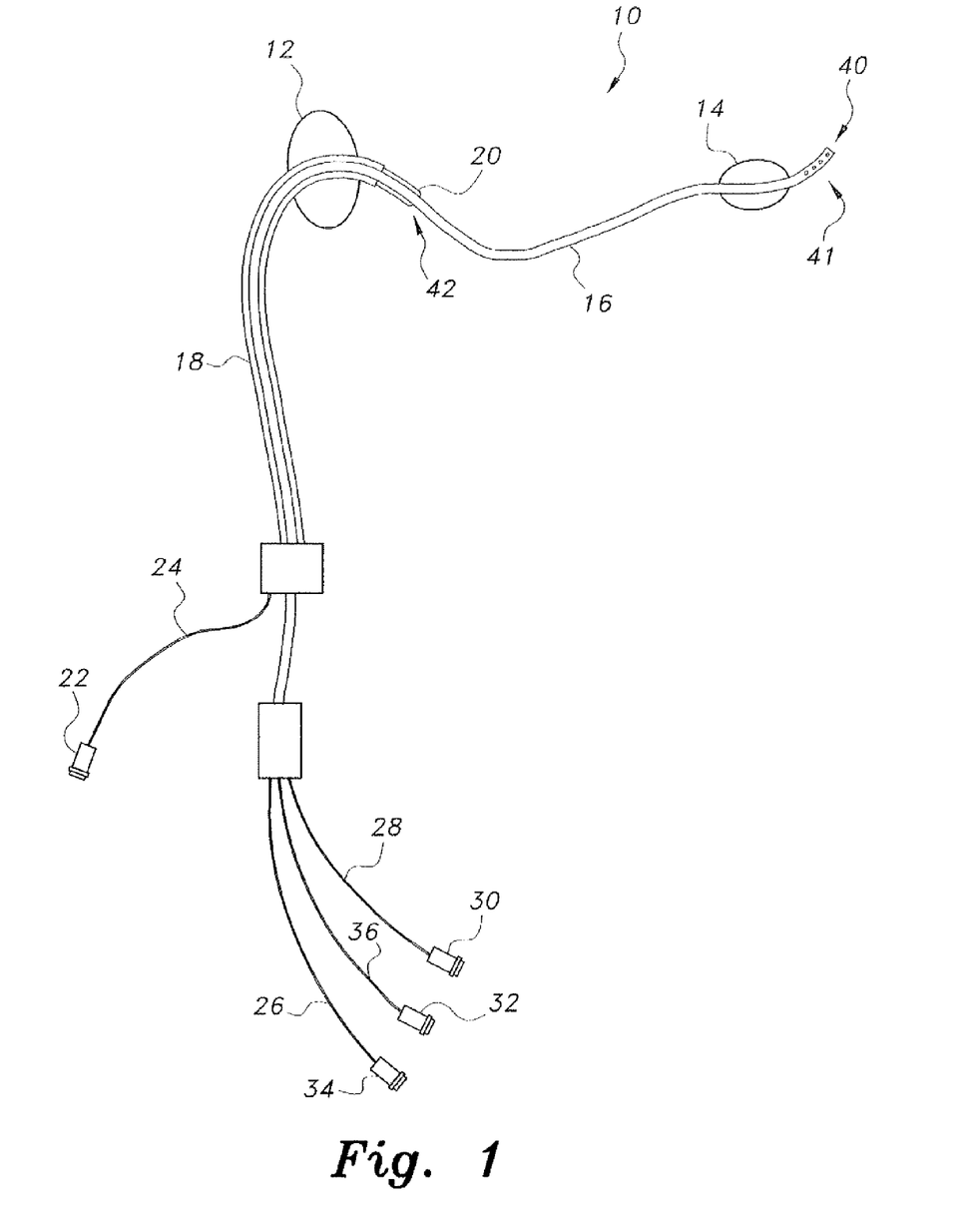
FIG. 1 diagrammatically illustrates a system for removing blood containing contrast dye according to the present invention.

The system and method for removing blood containing contrast dye relates to the removal of blood containing contrast dye solution from the coronary sinus of a patient's heart before the blood containing the dye enters the right atrium and circulates through the bloodstream to the kidneys, potentially causing contrast-induced nephropathy (CIN). As best shown in FIG. 1, the system for removing blood containing radiographic contrast media (dye) 10 includes an inner catheter 16 having a fixed proximal end and a free distal end, and an outer catheter 18 coaxially disposed around a portion of the inner catheter 16. The inner catheter 16 is partially disposed coaxially within the outer catheter 18, defining inner and outer channels. The fixed proximal end of the inner catheter 16 is positioned within the outer catheter 18 coincident with the proximal end of the outer catheter 18, and the distal end of the inner catheter 16 partially extends outward from the outer catheter 18. An annular suction orifice 42 is defined between an inner wall of the outer catheter 18 and an outer wall of the inner catheter 16.

A first balloon 12 is mounted on the outer catheter 18 adjacent the distal end of the outer catheter 18, and a second balloon 14 is mounted on the inner catheter 16 adjacent the distal free end 40 thereof. The distal free end 40 extends beyond the second balloon 14. As shown in FIG. 1, when inflated, the second balloon 14 is preferably smaller than the first balloon 12. As will be described below in greater detail, the first balloon 12 is dimensioned and configured to block or seal, when inflated, the ostium of the coronary sinus vein CS, and the second balloon 14 is dimensioned and configured to lodge against the inner wall of the coronary sinus vein CS to anchor the system 10 and form a seal for blood removal between the pair of balloons. The larger first balloon 12 preferably has a diameter of approximately 20-30 mm, and the smaller second balloon 14 preferably has a diameter of approximately 8-10 mm.

A first lumen 28 is in communication with the first balloon 12, and the first lumen 28 terminates in a first inflation port 30. Similarly, a second lumen 36 is in communication with the second balloon 14, and the second lumen terminates in a second inflation port 32. Alternatively, a single lumen may be used to inflate both balloons 12, 14 by attaching a three-way valve to the inflation port. In the first position, the valve would open the lumen to the second balloon 14 for inflation thereof, in a second position the valve would close the lumen to the second balloon and open the lumen to the first balloon 12 for inflation thereof, and in the third position the valve would open the lumen to both balloons for deflation of the balloons 12, 14.

A third lumen 26 is further in communication with the outer catheter 18 and the annular suction orifice 42 for draining blood through the outer channel from between the first and second balloons 12, 14. The third lumen 26 terminates in a first suction port 34. A guide wire may further be disposed within the third lumen 26, such as a conventional 0.035 inch guide wire or the like, for positioning the inner catheter 16 and outer catheter 18. The guide wire may then be removed once the guide wire contacts the wall of the coronary sinus CS, thus indicating proper positioning and initiating inflation of the balloons.

First and second inflation ports 30 and 32 may be connected to any suitable source of pressurized air or the like for selectively sequentially inflating first and second balloons 12, 14, as will be described in detail below. The first suction port 34 may be connected to a vacuum pump or the like for providing negative pressure through the third lumen 26, allowing for the draining of blood containing contrast dye solution through orifice 42 to avoid the risk of contrast-induced nephropathy.

A fourth lumen 24 is in communication with the inner catheter 16 for draining blood through the distal free end 40 and inner channel defined by the inner catheter 16. The fourth lumen 24 terminates in a second suction port 22. As shown in FIG. 1, a guide 20 may be provided for centering the inner catheter 16. The guide 20 may cover the annular suction orifice 42, but have a plurality of apertures therein to permit the contrast-containing blood to be suctioned into the annular suction orifice 42. The free end of outer catheter 18, which defines the suction orifice 42, may have the guide 20 integrally formed thereon. The second suction port 22 may also be connected to an external vacuum pump or the like for providing negative pressure through fourth lumen 24, which is in communication with inner catheter 16, allowing for the draining of blood containing contrast dye solution through the distal free end 40 of the inner catheter 16 to further avoid the risk of contrast-induced nephropathy.

Figure 2:
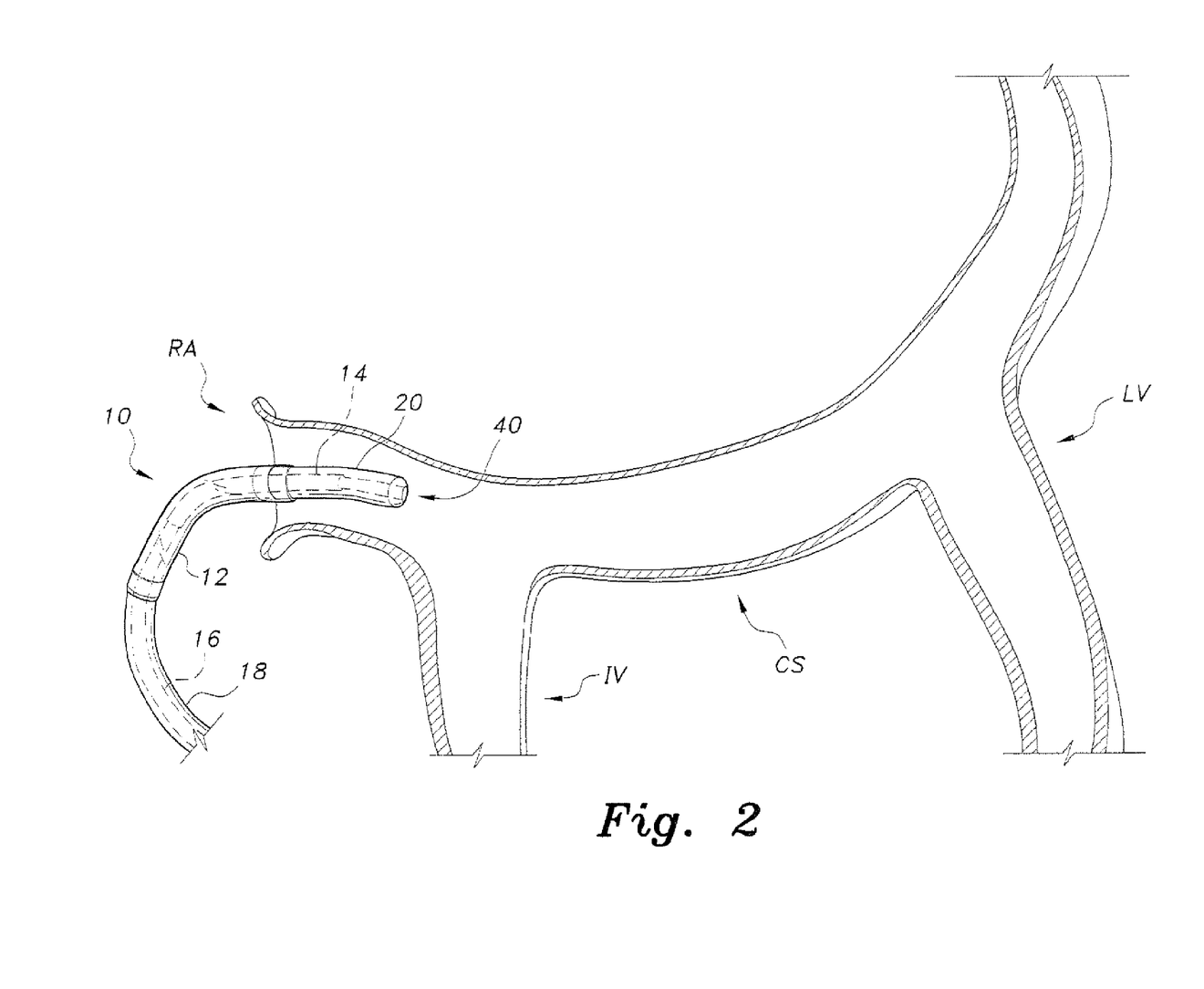
FIG. 2 is a schematic diagram showing the first step in a method for removing blood containing contrast dye, showing placement of the outer catheter in the ostium of the coronary sinus.
Figure 3:
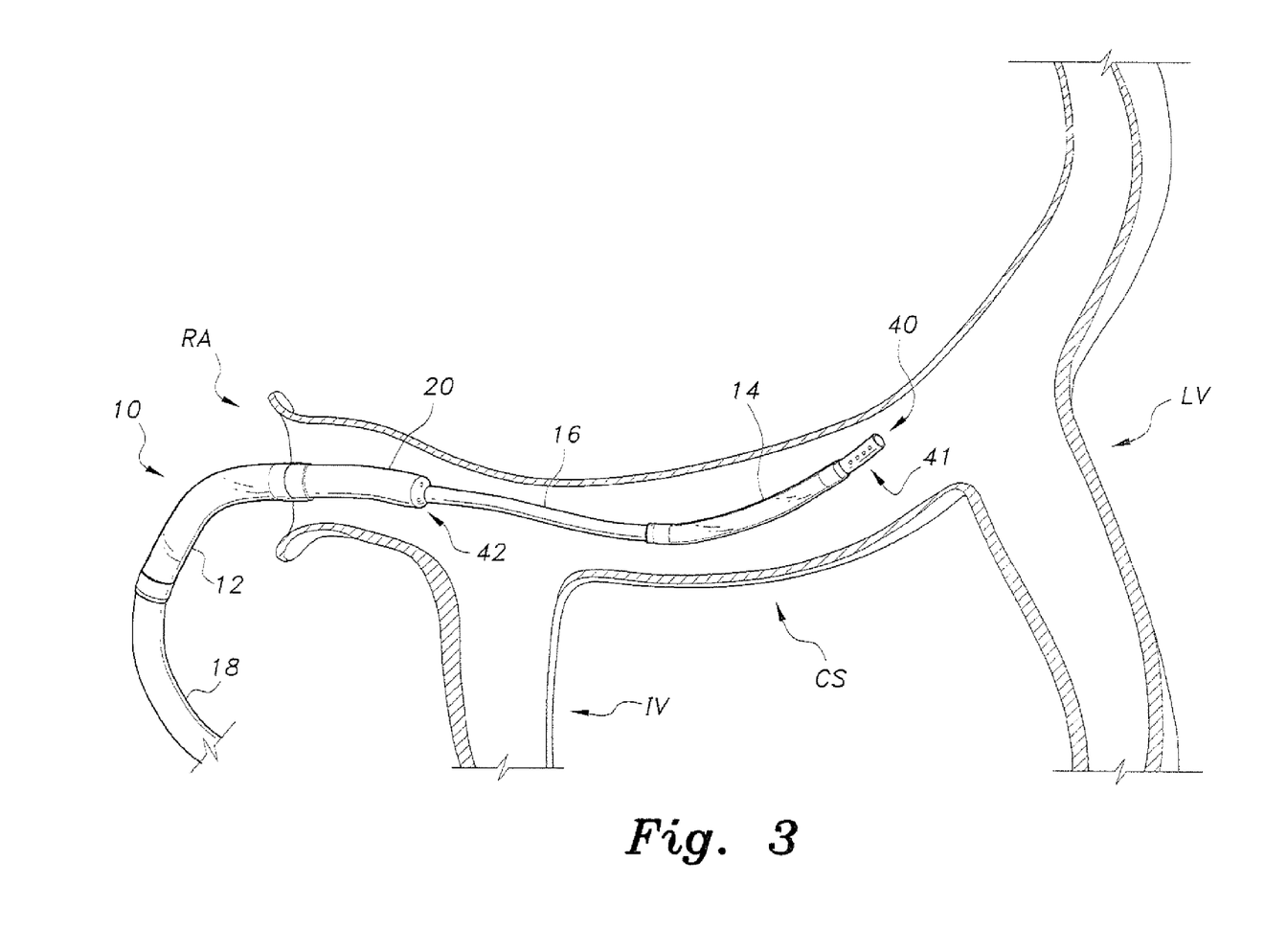
FIG. 3 is a schematic diagram showing the second step in a method for removing blood containing contrast dye, showing extension of the inner catheter into the coronary sinus between the posterior/inferior interventricular vein and the lateral vein.

In use, the first and second balloons 12, 14 are inflated after introducing a contrast dye solution D into a patient's blood stream, the second balloon being inflated first to anchor the system, the first balloon 12 then being inflated to seal the ostium of the coronary sinus CS, creating a vacuum between the two balloons. Blood containing the contrast solution dye is then removed from between the first and second balloons 12, 14. FIG. 2 illustrates the system 10 being initially inserted, with the outer catheter 18, which is used for positioning, being located in the patient's ostium. FIG. 3 shows the inner catheter 16 extended further along the patient's sinus, past the posterior inferior interventricular vein IV, and with the first balloon 12 being positioned in the right atrium RA. At this point, both balloons 12, 14 have not yet been inflated.

Figure 4:
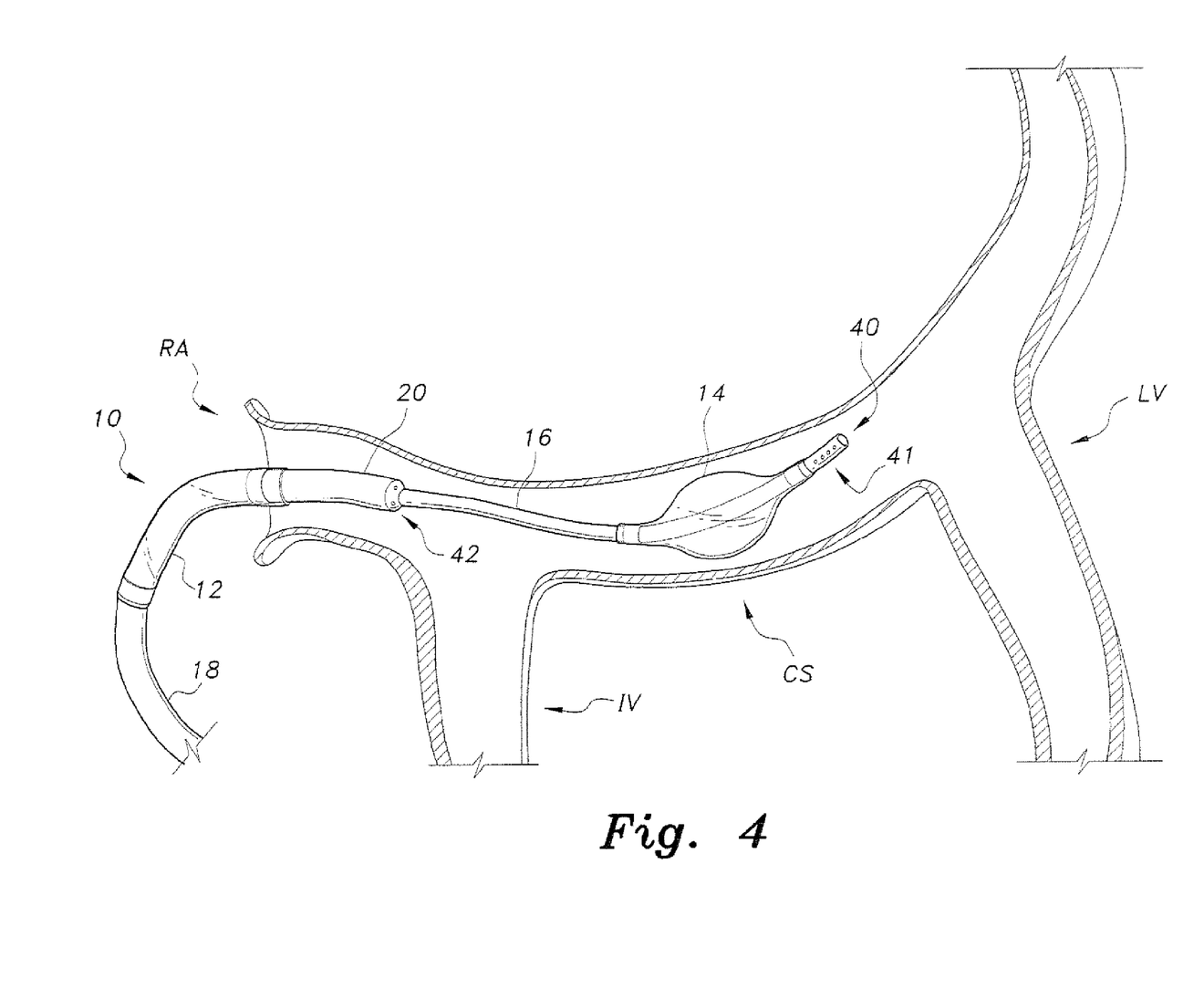
FIG. 4 is a schematic diagram showing the third step in a method for removing blood containing contrast dye, showing inflation of the second balloon in the coronary sinus vein to anchor the system.
Figure 7:
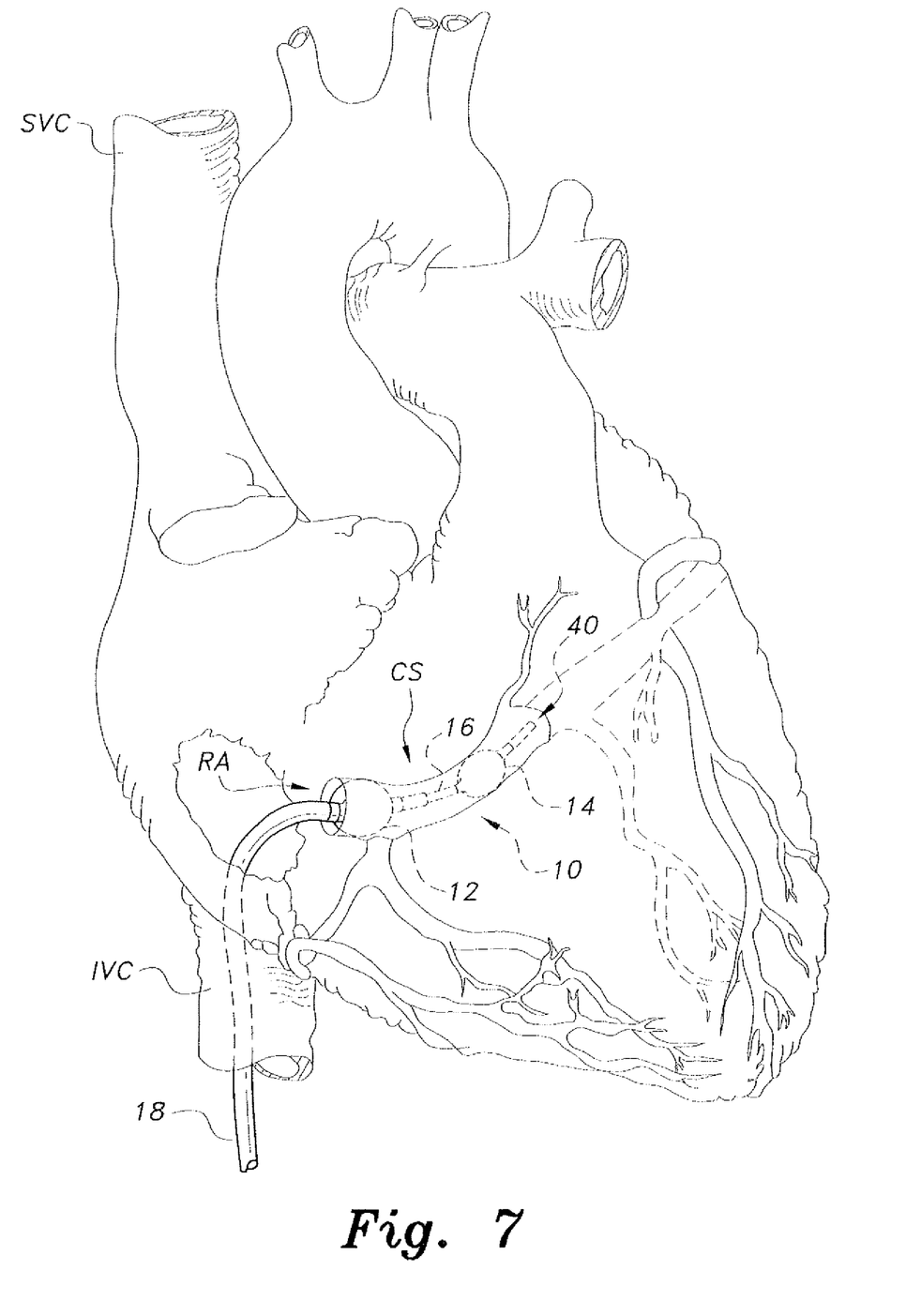
FIG. 7 diagrammatically illustrates the system for removing blood containing contrast dye in position within the patient's heart.
Figure 8:
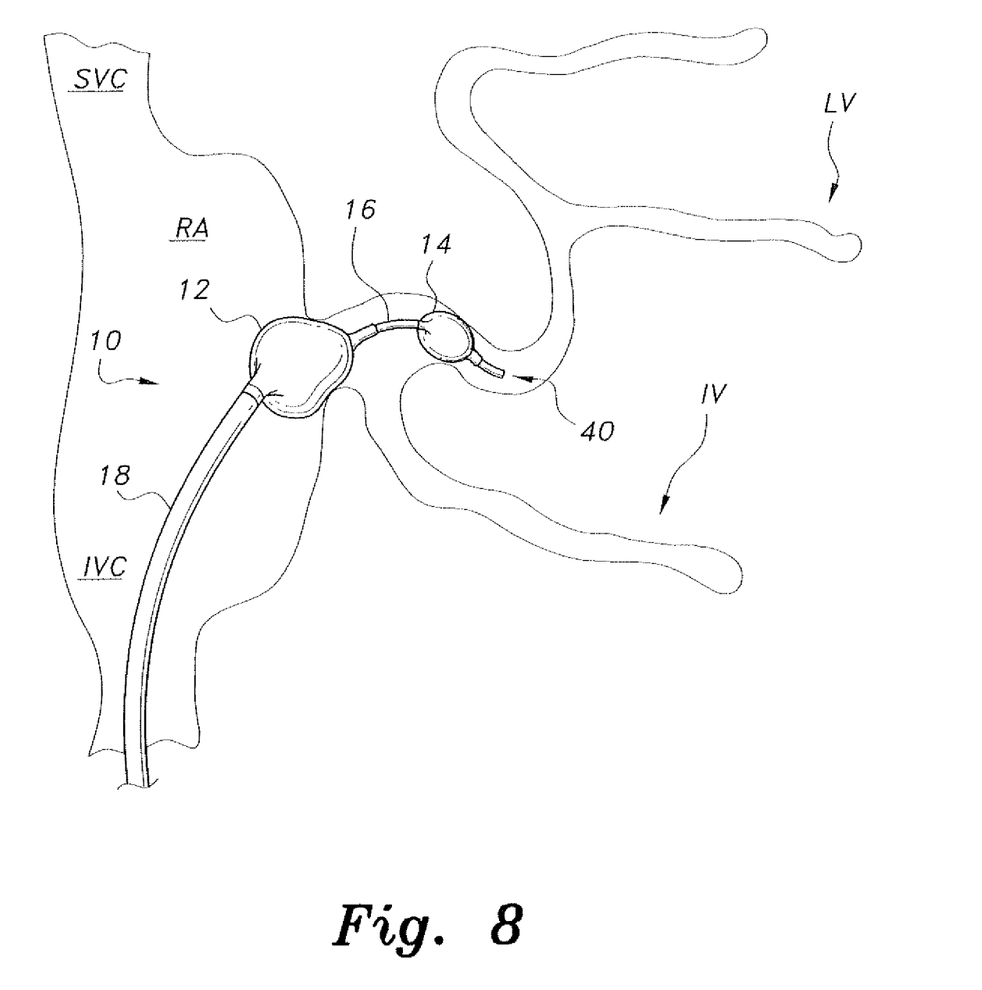
FIG. 8 diagrammatically illustrates the system for removing blood containing contrast dye positioned within the coronary sinus of the patient's heart.

In FIG. 4, the second balloon 14 is inflated first to anchor the inner catheter 16 in place in the patient's coronary sinus vein CS, with the distal free end 40 of the inner catheter 16 being positioned adjacent the patient's lateral vein LV. Preferably, the inner catheter 16 is formed from a softer material than the outer catheter 18, thus allowing the outer catheter 18 to be used for positioning (in the patient's ostium), and preventing damage to the inner wall of the coronary sinus vein CS. The second balloon 14, when inflated, blocks blood flow into the coronary sinus vein CS. As shown in FIGS. 7 and 8, the stiffer material forming the outer catheter 18 preferably maintains outer catheter 18 in a substantially inverted J-shape, allowing the outer catheter 18 to be positioned within the inferior vena cave (IVC) of the patient's heart, extending through the right atrium (RA) and into the coronary sinus (CS).

Figure 5:
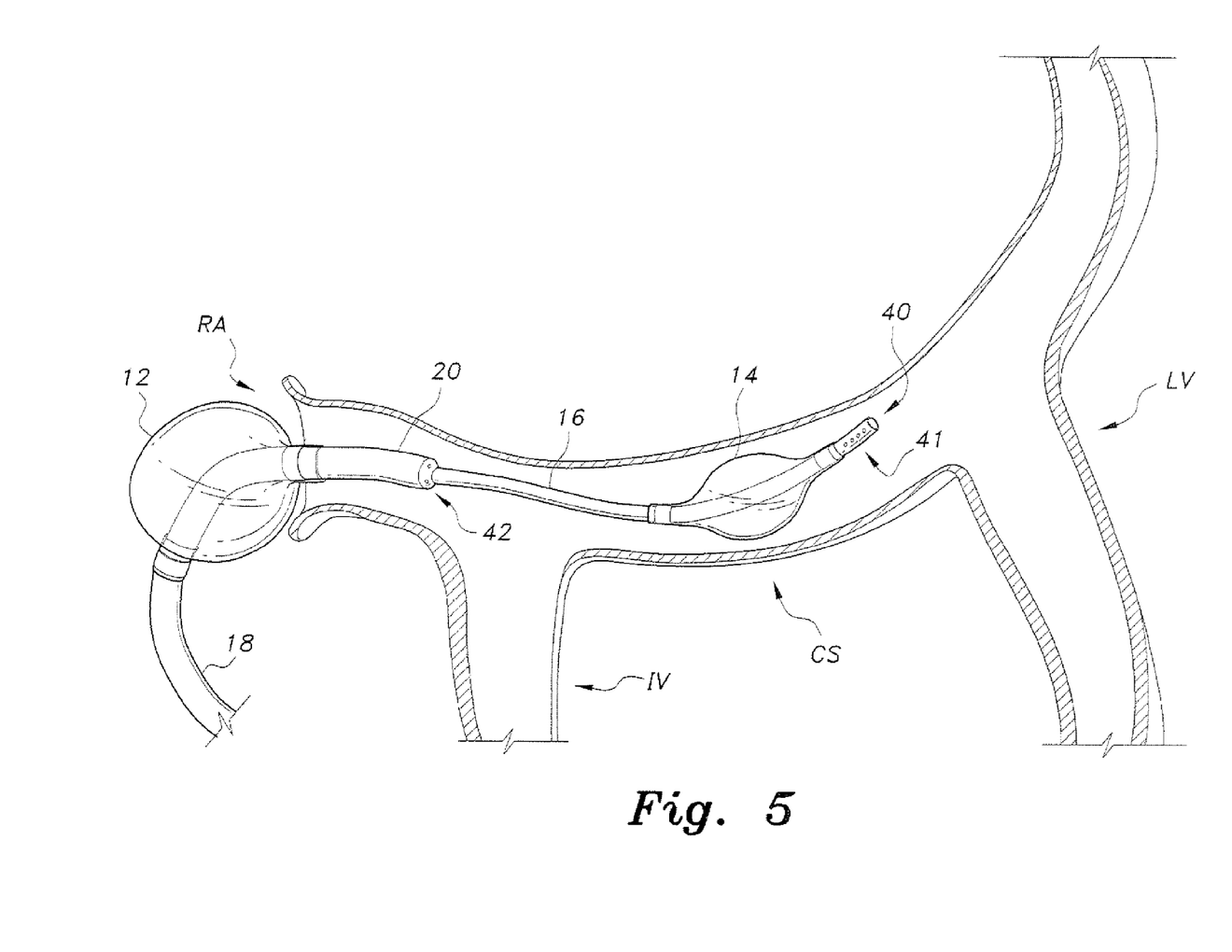
FIG. 5 is a schematic diagram showing the fourth step in a method for removing blood containing contrast dye, showing inflation of the first balloon in the right atrium to seal the ostium of the coronary sinus.
Figure 6:
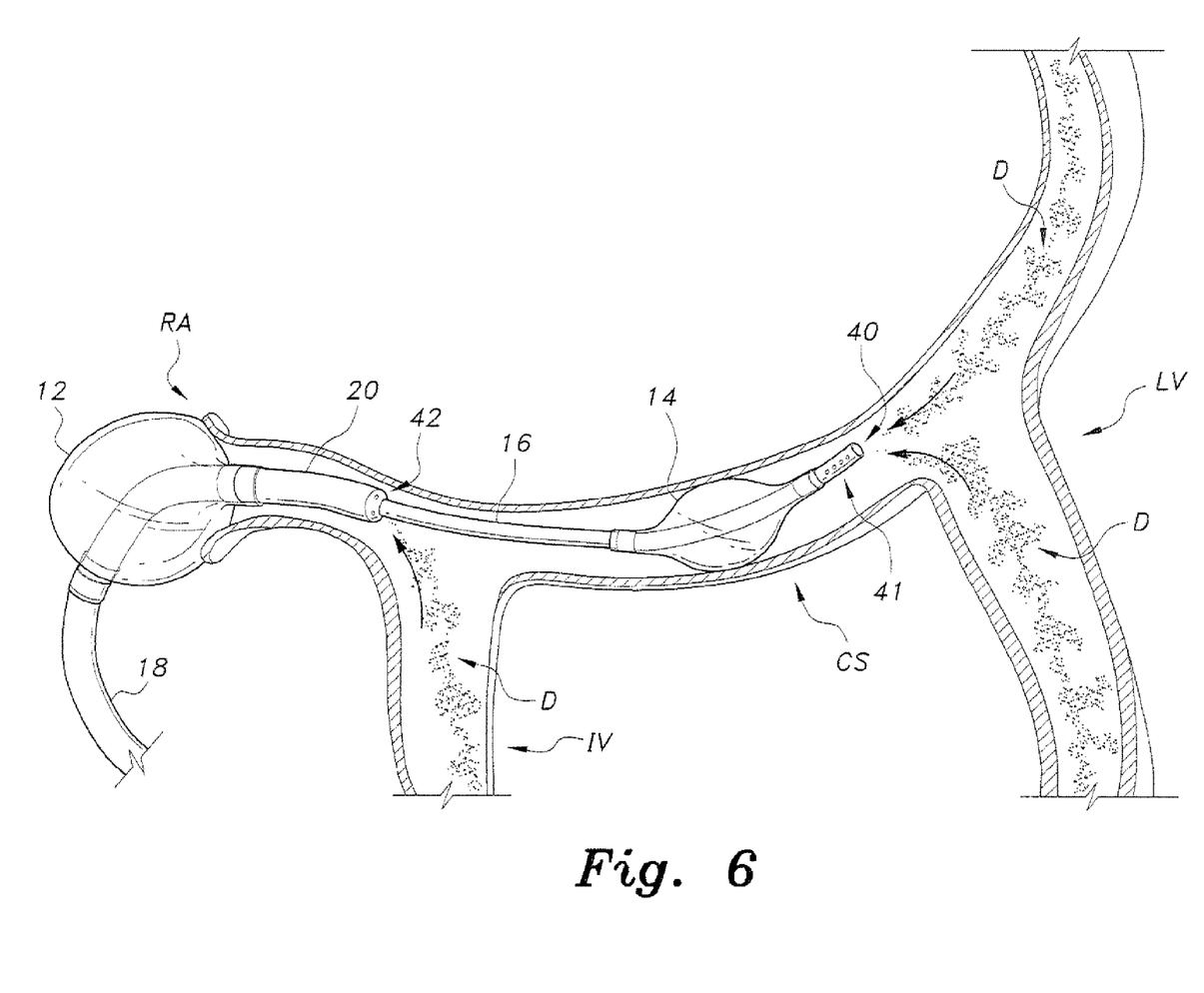
FIG. 6 is a schematic diagram showing the fifth step in a method for removing blood containing contrast dye, showing suction applied to remove blood containing contrast dye from between the two balloons through the outer lumen, and also suction applied to remove blood containing contrast dye distal to the inner catheter through the inner lumen.

As shown in FIG. 5, the first balloon 12 is then inflated to anchor the outer catheter 18 in place with respect to the patient's right atrium RA. The inflated first balloon 12 blocks blood flow from the coronary sinus to the right atrium RA during the procedure. As shown in FIG. 6, the blood containing the contrast dye solution D is then removed from between the inflated first and second balloons 12, 14 by suction through the annular suction orifice 42 into the annular outer channel. Contrast dye solution D is also removed distal to the inner catheter 16 by suction into the inner channel. The first and second balloons 12, 14 are deflated when the blood containing the contrast dye solution D from between the first and second balloons 12, 14 has been removed. For relatively long procedures, involving multiple injections of radiographic contrast media, the system 10 may further be connected to an external hemp filtration system, allowing the drained dye-containing blood to be filtered and then returned to the patient's bloodstream.

As shown, the system 10 acts as a closed circuit to remove the contrast dye solution D contaminated blood to prevent its arrival at the kidneys. Thus, the system 10 provides for avoidance of contrast-induced nephropathy in high risk patients. It should be noted that the distal free end 40 of the inner catheter 16 preferably has a plurality of openings or apertures 41 formed through the sidewall thereof. Thus, if free end 40 contacts the wall of the coronary sinus and becomes blocked, or is otherwise blocked, the blood containing the contrast dye D can still be suctioned through the openings or apertures 41.

It is to be understood that the present invention is not limited to the embodiments described above, but encompasses any and all embodiments within the scope of the following claims.

I claim:

1. A system for removing blood containing contrast dye, comprising:
    an inner catheter having a fixed proximal end and a distal free end;
    an outer catheter having a proximal end and a distal end, the inner catheter being partially coaxially disposed within the outer catheter defining an annual outer channel between the inner catheter and the outer catheter, the fixed proximal end of the inner catheter being coincident with the proximal end of the outer catheter, the inner catheter partially extending outward from the distal end of the outer catheter defining an annular suction orifice between an inner wall of the distal end of the outer catheter and an outer wall of the inner catheter;
    a first balloon mounted on the outer catheter adjacent the distal end of the outer catheter;
    a second balloon mounted on the inner catheter adjacent the distal free end thereof, the distal free end extending beyond the second balloon;
    a first lumen in communication with the first balloon, the first lumen having a first inflation port;
    a second lumen in communication with the second balloon, the second lumen having a second inflation port;
    a third lumen in communication with the annular outer channel and the annular suction orifice for draining blood from between the first and second balloons, the third lumen having a first suction port, wherein the annular suction orifice includes a guide covering the annular suction orifice, the guide centering the inner catheter and having a plurality of apertures defined therein communicating with the annular suction orifice; and
    a fourth lumen in communication with the inner catheter for draining blood through the distal free end of the inner catheter and the inner channel, the fourth lumen having a second suction port.

2. The system for removing blood containing contrast dye as recited in claim 1, further comprising a guide wire disposed within the third lumen.

3. The system for removing blood containing contrast dye as recited in claim 1, wherein said second balloon is smaller than said first balloon.

4. The system for removing blood containing contrast dye as recited in claim 1, wherein said inner catheter is formed from a softer material than said outer catheter.

5. The system for removing blood containing contrast dye as recited in claim 1, wherein the distal free end of the inner catheter has a plurality of apertures formed through a sidewall thereof.

6. A method for removing blood containing contrast dye during coronary angioplasty, comprising the steps of:
    providing an inner catheter having a fixed proximal end and a distal free end;
    providing an outer catheter having a proximal end and a distal end, the inner catheter being partially coaxially disposed within the outer catheter defining an annual outer channel between the inner catheter and the outer catheter, the fixed proximal end of the inner catheter being coincident with the proximal end of the outer catheter, the inner catheter partially extending outward from the distal end of the outer catheter defining an annular suction orifice between an inner wall of the distal end of the outer catheter and an outer wall of the inner catheter;
    providing a guide centering the inner catheter within the outer catheter, the guide having a plurality of apertures defined therein communicating with the annular suction orifice;
    providing a first balloon mounted on the outer catheter adjacent the distal end of the outer catheter;

providing a second balloon mounted on the inner catheter adjacent the distal free end of the inner catheter, the distal free end extending beyond the second balloon;

inflating the second balloon first to anchor the inner catheter in place in a patient's coronary sinus vein with the distal free end thereof positioned adjacent the patient's lateral vein;

inflating the first balloon secondly to anchor the outer catheter to seal the ostium of the patient's coronary sinus vein;

removing blood containing contrast dye from between the first and second balloons by suction through the plurality of apertures of the annular suction orifice;

removing a second volume of blood containing contrast dye from the patient's coronary sinus vein distal through the distal free end of the inner catheter; and deflating the first and second balloons when the blood containing the contrast solution between the first and second balloons has been removed.

7. The method for removing blood containing contrast dye as recited in claim 6, further comprising the step of hemofiltering the patient's blood and returning the hemo filtered blood to the patient's bloodstream.

8. The system for removing blood containing contrast dye as recited in claim 6, further comprising the step of providing a guide wire disposed within the third lumen.

9. The system for removing blood containing contrast dye as recited in claim 6, wherein the second balloon is smaller than said first balloon.

10. The system for removing blood containing contrast dye as recited in claim 6, wherein the distal free end of the inner catheter has a plurality of apertures formed through a sidewall thereof.

* * * * *